United States Patent [19]

Asato

[11] 3,972,895
[45] Aug. 3, 1976

[54] BENZOTHIENYLISOTHIOCYANATES
[75] Inventor: Goro Asato, Titusville, N.J.
[73] Assignee: American Cyanamid Company, Stamford, Conn.
[22] Filed: Aug. 11, 1975
[21] Appl. No.: 603,465

Related U.S. Application Data
[62] Division of Ser. No. 458,272, April 5, 1974, Pat. No. 3,944,567.

[52] U.S. Cl............................ 260/329 S; 260/332.5; 424/275; 71/90
[51] Int. Cl.$^2$......................................... C07D 333/00
[58] Field of Search.......... 260/329 S, 329 F, 330.5, 260/332.5

[56] References Cited
OTHER PUBLICATIONS
Hartough, "Chem. of Heterocyclic Compounds" (condensed thiophenes) (1954) p. 37.

Primary Examiner—James O. Thomas, Jr.
Assistant Examiner—A. Siegel
Attorney, Agent, or Firm—Denis A. Polyn

[57] ABSTRACT

This invention relates to 4,5,6,7-tetrahydrobenzo[b]-thien-4-yl isothiocyanates and methods for the preparation thereof. These compounds are useful in the manufacture of substituted urea derivatives which are useful as animal growth regulants and herbicides.

7 Claims, No Drawings

BENZOTHIENYLISOTHIOCYANATES

SUMMARY OF THE INVENTION

This invention relates to 4,5,6,7-tetrahydrobenzo[b]-thien-4-yl isocyanates and isothiocyanates represented by the formula:

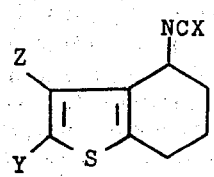

wherein X is a member selected from the group consisting of sulfur and oxygen; Y is a member selected from the group consisting of hydrogen, halogen, cyano, alkyl $C_1$–$C_4$ and methyl carbonyl; and Z is a member selected from the group consisting of hydrogen and alkyl $C_1$–$C_4$. The invention also relates to a method for the preparation of the above-said compounds.

In accordance with this invention, the above-identified isocyanates can be prepared by reacting the appropriate 4,5,6,7-tetrahydrobenzo[b]thien-4-amine or amine salt with phosgene, preferably under anhydrous conditions, e.g., a blanket of inert gas such as nitrogen. The reaction with the amine is initially carried out at a temperature between about 0°C. and 40°C., preferably 10°C. to 20°C., and then heated to between about 50°C. and 100°C., and preferably from 60°C. to 80°C., while the reaction of the amine salt is carried out between 50°C. and 150°C., and preferably at 100°C. to 120°C. The reaction is usually also conducted in the presence of an organic solvent such as hydrocarbons, benzene, toluene, xylene, chlorobenzene or other chlorinated hydrocarbons.

solvent such as tetrahydrofuran or an ether such as diethyl ether, at a temperature between about −10°C. and +80°C., and preferably between −10°C. and +50°C. The product can be isolated by distillation or by dry-column chromatography, and the reaction may be illustrated as follows:

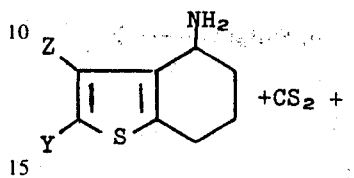

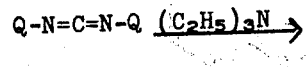

wherein Q is cyclohexyl, cycloheptyl or alkyl $C_4$–$C_6$.

Alternatively, the isothiocyanate can also be prepared by the reaction of 1,1'-thiocarbonyldiimidazole with 4,5,6,7-tetrahydrobenzo[b]thien-4-amine in the presence of a solvent such as methylene chloride, tetrahydrofuran, ethyl acetate, chlorobenzene or chlorinated hydrocarbons such as chloroform at ambient temperature, or between about 20°C. to 100°C., and preferably between 20°C. and 80°C. The reaction may be illustrated as follows:

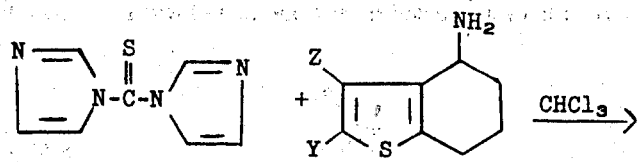

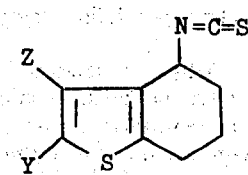

The isothiocyanate of the above formula can be prepared by reacting the appropriate 4,5,6,7-tetrahydrobenzo[b]thien-4-amine with equimolar amounts of carbon disulfide, triethylamine, and a carbodiimide represented by the formula: Q—N=C=N—Q, where Q is cyclohexyl, cycloheptyl, alkyl $C_4$–$C_6$, or the like. This reaction is generally conducted in the presence of a These 4,5,6,7-tetrahydrobenzo[b]thien-4-yl isocyanates and isothiocyanates can be converted to 4,5,6,7-tetrahydrobenzo[b]thien-4-ylurea compounds which are highly effective as animal growth regulants and herbicidal agents.

Conversion of said isocyanates and isothiocyanates to said 4,5,6,7-tetrahydrobenzo[b]thien-4-ylureas can be achieved by reacting approximately equimolar amounts of an appropriately substituted 4,5,6,7-tetrahydrobenzo[b]thien-4-yl isocyanate or isothiocyanate and an appropriately substituted amine. The reaction can be graphically illustrated as follows:

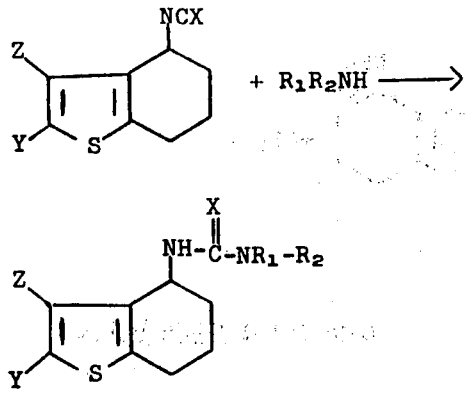

wherein X is sulfur or oxygen; Y is a member selected from the group consisting of hydrogen, halogen, cyano, alkyl $C_1$–$C_4$ and methyl carbonyl; Z represents a member selected from the group consisting of hydrogen and alkyl $C_1$–$C_4$; $R^2$ is a member selected from the group consisting of hydrogen, alkyl $C_1$–$C_{12}$, cycloalkyl $C_3$–$C_6$, allyl, methallyl, 2-butenyl,

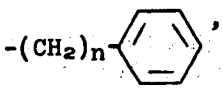

benzyloxyl, hydroxyl, alkoxyl $C_1$–$C_4$ and propargyl; $R_1$ is a member selected from the group consisting of hydrogen, alkyl $C_1$–$C_6$, cycloalkyl $C_3$–$C_6$ and

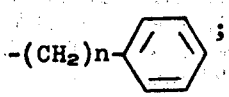

$n$ is an integer selected from 1 and 2, and when

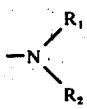

is taken together it is morpholino, piperidino or pyrrolidino.

In practice, the reaction is usually conducted with a slight excess (i.e., up to 20% excess) of the amine in the presence of a solvent, such as described above. Although the reaction may be conducted at superatmospheric pressure and temperatures as high as 100°C., it is generally preferable to conduct the reaction at atmospheric pressure at a temperature between 0°C. and 80°C.

As indicated, the 4,5,6,7-tetrahydrobenzo[b]thien-4-yl isocyanates and isothiocyanates of this invention are useful in the manufacture of substituted urea derivatives which are growth-promoting agents for animals such as poultry, fur-bearing and farm animals; and use of said growth-promoting agents also provides the added advantage of improving feed conversion for said animals.

In practice, a growth-promoting amount of a 4,5,6,7-tetrahydrobenzo[b]thien-4-ylurea is administered to a host animal usually in, or with, the animal's feed. However, said compound may also be administered as a subcutaneous implant under the skin of said animal or as a parental injection. When administered in the feed of chickens, turkeys, sheep, cattle, goats, and the like, usually about 0.0001% to 0.08% by weight, and preferably 0.001% to 0.04% by weight of the 4,5,6,7-tetrahydrobenzo[b]thien-4-ylurea, is effective for increasing growth rate and improving feed conversion. When administered to said animals as a parenteral injection or subcutaneous implant, usually in amounts that will supply about 0.001 mg. to 0.2 mg., and preferably 0.005 mg. to 0.10 mg. per kg. of body weight per day of the active compound, said compound will produce the desired improvement in weight gain and enhance feed conversion.

In tests conducted with day-old chicks, it was found that from 1 ppm. to 9 ppm. of 4,5,6,7-tetrahydrobenzo[b]thien-4-ylurea, administered in the chick feed, produced a 3.3% to 6.6% improvement in weight gain over untreated controls, and likewise produced a 2.7% to 4.7% improvement in feed conversion. This utility is further described in my copending application Ser. No. 436,826, filed Jan. 25, 1974 now abandoned.

The 4,5,6,7-tetrahydrobenzo[b]thien-4-ylurea prepared from the isocyanates and isothiocyanates of this invention are also useful as herbicidal agents. They are effective for controlling undesirable broadleaf and grass weeds when applied to soil containing seeds of said undesirable weeds, or when applied to the foilage of such plants. Usually about 5 pounds to 15 pounds, and preferably about 8 pounds to 10 pounds per acre of the active compound, is sufficient to provide control of the undesirable plants.

SPECIFIC DISCLOSURE OF THE INVENTION

This invention is further illustrated by the following examples which describe the preparation of the present compounds, their conversion to active compounds and the testing thereof.

EXAMPLE 1

Preparation of
4,5,6,7-Tetrahydrobenzo[b]thien-4-ylisocyanate

A sample of 47.6 grams of 4,5,6,7-tetrahydrobenzo[b]thien-4-amine hydrochloride is stirred in 150 ml. of water, and 350 ml. of 10% sodium hydroxide is added. The mixture is shaken and extracted with benzene twice. The extract is dried and evaporated to dryness to afford the amine, which is stored under nitrogen. The amine is then added dropwise to 866 ml. of 12.5% phosgene solution (benzene) in nitrogen atmosphere at 20°C. After stirring for an hour at room temperature, the mixture is gradually heated to 60°C. and kept at this temperature for 7 hours. The mixture is cooled to room temperature and evaporated to dryness to afford a residue, which is distilled to give 22.4 grams, boiling point 98°C. to 101°C./0.6 Torr., of 4,5,6,7-tetrahydrobenzo[b]thien-4-yl isocyanate.

The reaction may also be carried out in toluene, xylene, chlorobenzene and chlorinated hydrocarbons.

Alternatively, 5.7 grams of 4,5,6,7-tetrahydrobenzo[b]thien-4-amine hydrochloride is stirred in 20 ml. of toluene at 97°C., and phosgene is slowly introduced into the mixture via a capillary delivery tube. The mixture is heated to reflux temperature, and the flow of phosgene is continued until most of the amine hydrochloride disappears. The mixture is then filtered to remove unreacted amine hydrochloride, and the filtrate is evaporated to dryness under reduced pressure to give the 4,5,6,7-tetrahydrobenzo[b]thien-4-yl isocyanate.

EXAMPLES 2 through 8

Using the procedure described in Example 1, and substituting the proper 4,5,6,7-tetrahydrobenzo[b]thien-4-amine hydrochloride, the following isocyanates are prepared:

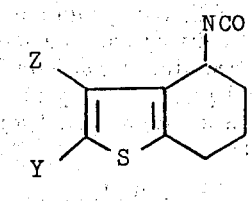

| Example | Z | Y |
|---|---|---|
| 2 | H | CH |
| 3 | CH₃ | H |
| 4 | CH₃ | CH₃ |
| 5 | H | CH₃CO— |
| 6 | H | Br |
| 7 | H | CN |
| 8 | H | Cl |

EXAMPLE 9

Preparation of 4,5,6,7-Tetrahydrobenzo[b]thien-4-ylisothiocyanate

Method A

A sample (47.5 grams) of 4,5,6,7-tetrahydrobenzo[b]thien-4-ylamine hydrochloride is stirred in methylene chloride/water, and 5% sodium hydroxide solution is added gradually until the pH is about 10. The methylene chloride layer is removed, and the aqueous layer is extracted with methylene chloride. The organic layers are combined, dried over magnesium sulfate, and evaporated to dryness to afford the oily amine. The amine is stirred in 500 ml. of ethyl acetate under nitrogen atmosphere, and 25.4 grams of triethylamine is added. After about 15 minutes, 20.9 grams of carbon disulfide is added to give a copious precipitate. An additional 200 ml. of ethyl acetate is added, and the solid is pulverized with a spatula. After an hour of stirring, 51.5 grams of dicyclohexylcarbodiimide is added, and stirring continued for an overnight period. Subsequently, the mixture is heated at about 50°C. for 2 hours and cooled. The solid is removed by filtration and washed with ethyl acetate. The filtrate is evaporated to afford a mixture of solid and mostly oil. The solid is removed by filtration after ether is added. The ether filtrate is evaporated to dryness to afford the crude isothiocyanate, which is purified by chromatography on a dry-column of silica gel using 65/35 (volume/volume) of petroleum ether/methylene chloride. Other higher boiling alkyl esters of aliphatic acids, dimethoxyethane, tetrahydrofuran, diethyl ether, diethylene glycol dimethyl ether, and other inert solvents may be used as solvents.

Method B

The same isothiocyanate is obtained by allowing equivalent quantities of the benzothiophene amine and 1,1'-thiocarbonyldiimidazole to react in chloroform or methylene chloride at room temperaure for an hour. Evaporation of the solvent gives 4,5,6,7-tetrahydrobenzo[b]thien-4-ylisothiocyanate and imidazole. Other inert solvents such as chlorinated hydrocarbons, ethyl acetate, tetrahydrofuran and dimethoxyethane, may be used.

EXAMPLES 10 through 16

In the manner described in Example 9, using the proper 4,5,6,7-tetrahydrobenzo[b]substituted thien-4-ylamine hydrochloride, the following isothiocyanates are prepared:

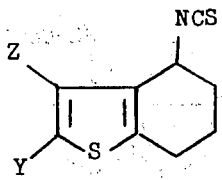

| Example | Z | Y |
|---|---|---|
| 10 | H | CH₃ |
| 11 | CH₃ | H |
| 12 | CH₃ | CH₃ |
| 13 | H | CH₃CO— |
| 14 | H | Br |
| 15 | H | CN |
| 16 | H | Cl |

EXAMPLE 17

Preparation of 1-Methoxy-3-(4,5,6,7-tetrahydrobenzo[b]thien-4-yl)urea

A mixture of 5 grams of methoxyamine hydrochloride in 60 ml. of methylene chloride is stirred and cooled to 15°C., and 6 grams of triethylamine in 15 ml. of methylene chloride is added. After 20 minutes of stirring, 5.38 grams of 4,5,6,7-tetrahydrobenzo[b]thien-4-yl isocyanate is added dropwise. After stirring an additional 0.5 hour at 15°C. to 20°C., the mixture is stirred at room temperature for 0.5 hour. The mix is then filtered, and the filtrate is washed with water and saturated sodium bicarbonate solution. The filtrate is dried (magnesium sulfate) and evaporated to dryness to afford the title compound which is recrystallized from acetone/hexane to give the product with melting point 138.5°C. to 141°C.

EXAMPLES 18 through 24

The following ureas are prepared in the manner described in Example 17 by using the desired 4,5,6,7-tetrahydro[b]substituted thien-4-yl isocyanate with the proper amine hydrochloride.

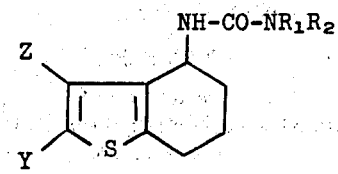

| Example | R₁ | R₂ | Z | Y | Melting Point °C. |
|---|---|---|---|---|---|
| 18 | H | C₂H₅ | H | CH₃ | 205–208 |
| 19 | H | sec-C₄H₉ | CH₃ | H | 196–198 |
| 20 | H | sec-C₄H₉ | CH₃ | CH₃ | 181–183.5 |
| 21 | H | H | H | CH₃CO— | 218–220 |
| 22 | H | H | H | Cl | 194–198 |
| 23 | H | H | H | CN | 210–214 |
| 24 | H | H | H | Br | 206.5–209.5 |

EXAMPLES 25 through 29

The following compounds were prepared by allowing equivalent amounts of the appropriate amines to react with the corresponding isothiocyanates in methylene chloride, ethanol or benzene.

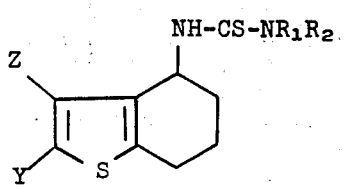

| Example | R₁ | R₂ | Z | Y | melting Point °C. |
|---|---|---|---|---|---|
| 25 | H | C₂H₅ | H | CH₃ | 116–118.5 |
| 26 | H | C₂H₅ | CH₃ | H | 121–125 |
| 27 | H | C₂H₅ | CH₃ | CH₃ | 153–157 |
| 28 | H | C₂H₅ | H | H | 111–117 |
| 29 | H | OCH₃ | CH₃ | H | 74–77 |

EXAMPLE 30

Preparation of 2-Chloro-4,5,6,7-tetrahydrobenzo[b]thien-4-amine

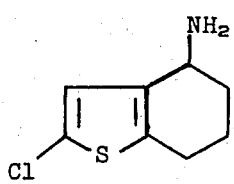

A sample of 11.4 grams of 4,5,6,7-tetrahydrobenzo[b]thien-4-amine hydrochloride is stirred in 150 ml. of chloroform at about 10°C., and 6.1 ml. of sulfuryl chloride is added dropwise. The mixture is stirred for 3.5 hours at room temperature, and then about 20 ml. of 50% sodium hydroxide solution is added gradually to dissolve the suspended solid. The mixture is then poured into water and extracted with chloroform twice. The extracts are dried, evaporated to dryness, and the residue is distilled to give 7.4 grams of 2-chloro-4,5,6,7-tetrahydrobenzo[b]thien-4-amine, boiling point 94°C. to 98°C./0.5 Torr.

EXAMPLE 31

Preparation of N-(2-Acetyl-4,5,6,7-tetrahydrobenzo[b]thien-4-yl)acetamide

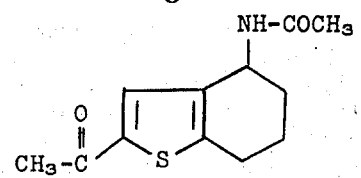

N-Acetyl-4,5,6,7-tetrahydrobenzo[b]thien-4-amine (19.5 grams) is stirred in 300 ml. of methylene chloride in nitrogen atmosphere, and 17 ml. of acetyl chloride is added. The mixture is cooled to about 10°C., and 28.1 ml. of stannic chloride is added slowly. After stirring for 1.5 hours at room temperature, the mixture is cooled to about 10°C., and 450 ml. of 1.2N hydrochloric acid is added. The mixture is shaken, and the methylene chloride solution is separated and washed with 1N hydrochloric acid, followed by saturated sodium bicarbonate solution. On drying and evaporating to dryness, crystals are obtained. Recrystallization from acetone/hexane gives 15.4 grams, melting point 167.5°C. to 172°C., of N-(2-acetyl-4,5,6,7-tetrahydrobenzo[b]thien-4-yl)acetamide.

EXAMPLE 32

Preparation of 2-Acetyl-4,5,6,7-tetrahydrobenzo[b]thien-4-amine hydrochloride

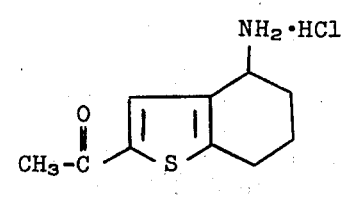

The product from Example 31, N-(2-acetyl-4,5,6,7-tetrahydrobenzo[b]thien-4-yl)acetamide (7.25 grams), is heated with 90 ml. of 1N hydrochloric acid at reflux temperature for 8.5 hours and cooled. The mixture is diluted with water and extracted with methylene chloride. The aqueous layer is then evaporated to dryness using 2-propanol for facilitating removal of water. This gives 4.85 grams of 2-acetyl 4,5,6,7-tetrahydrobenzo[b]thien-4-amine hydrochloride.

EXAMPLE 33

Preparation of 2-Cyano-N-formyl-4,5,6,7-tetrahydrobenzo[b]thien-4-amine

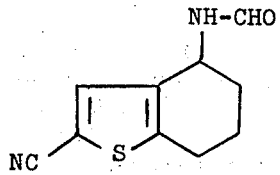

A mixture of 40.9 grams of 2-bromo-N-formyl-4,5,6,7-tetrahydrobenzo[b]thien-4-amine, 16.2 grams of cuprous cyanide and 47 ml. of dry dimethylformamide is heated at reflux temperature for 4 hours, and then cooled to about 60°C. and poured into 270 ml. of water. The mixture is extracted with toluene several times, and the toluene extracts are washed with 1.2N hydrochloric acid and saturated sodium chloride, respectively. On drying, 5.7 grams of crude product is obtained. The aqueous mother liquor is treated with 97.3 grams of ferric chloride hexahydrate and 30 ml. of concentrated hydrochloric acid and shaken. It is then extracted with toluene several times, and the extracts are washed further with 1.2N hydrochloric acid, saturated sodium bicarbonate solution and brine, respectively. On drying and evaporation of toluene, an additional 2.5 grams of product is obtained. The two crops are combined and recrystallized from acetone/hexane to afford 4.8 grams of 2-cyano-N-formyl-4,5,6,7-tetrahydrobenzo[b]thien-4-amine, melting point 131°C. to 134°C.

EXAMPLE 34

Preparation of 2-Cyano-4,5,6,7-tetrahydrobenzo[b]thien-4-amine hydrochloride

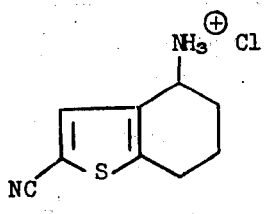

A mixture of 4.8 grams of 2-cyano-N-formyl-4,5,6,7-tetrahydrobenzo[b]thien-4-amine in 70 ml. of 1N hydrochloric acid is refluxed for an hour and evaporated to dryness to afford 4.7 grams of 2-cyano-4,5,6,7-tetrahydrobenzo[b]thien-4-amine hydrochloride, melting point 241°C. to 246°C. (dec.).

EXAMPLE 35

Preparation of 2-Bromo-N-formyl-4,5,6,7-tetrahydrobenzo[b]thien-4-amine

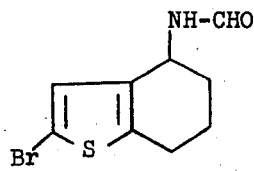

A sample of 54.3 grams of N-formyl-4,5,6,7-tetrahydrobenzo[b]thien-4-amine is stirred in 270 ml. of acetic acid and 90 ml. of water. Bromine (53 grams) in 120 ml. of acetic acid is added gradually. After stirring for 0.5 hour at room temperature, 61.5 grams of sodium acetate in 225 ml. of water is added. More water is added, and the mixture is extracted with ether. Methylene chloride is added to the ether solution to prevent crystallization, and the solution is evaporated to dryness. The residue is crystallized from acetone/hexane/ether to give 61 grams, melting point 104°C. to 108°C., of 2-bromo-N-formyl-4,5,6,7-tetrahydrobenzo[b]thien-4-amine.

EXAMPLE 36

Preparation of 2-Bromo-4,5,6,7-tetrahydrobenzo[b]thien-4-amine hydrochloride

Acid hydrolysis of 2-bromo-N-formyl-4,5,6,7-tetrahydrobenzo[b]thien-4-amine (Example 35) with 1 N hydrochloric acid after refluxing for one hour and evaporating to dryness affords 2-bromo-4,5,6,7-tetrahydrobenzo[b]thiophen-4-amine hydrochloride.

EXAMPLES 37 through 39

This general procedure is used to prepare the following amines.

The benzo[b]thiophen-4(5H)-one (13 mm.) is dissolved in 65 mm. of formamide, and 1.52 ml. of 97% formic acid is added. The mixture is stirred, heated to 160°C. for several hours, and analyzed by gas-liquid chromatography for completion of the reaction. After the required time of heating, the mixture is cooled to 50°C. and poured into water. The resulting crystals are then collected, washed with water, and dried. The product, N-(4,5,6,7-tetrahydro-substituted benzo[b]-thien-4-yl)formamide, is then hydrolyzed with 1N hydrochloric acid for 1 to 2 hours; the mixture is cooled, extracted with methylene dichloride, and after evaporating to dryness under reduced pressure, affords the crystalline amine hydrochloride.

| Example | Compound | Melting Point °C. |
|---|---|---|
| 37 | NH₂.HCl (structure) | 241–242 (dec.) |
| 38 | NH₂.HCl (structure) | 199–204 |
| 39 | NH₂.HCl (structure) | 245–248 (dec.) |

EXAMPLE 40

Mouse Growth Regulant Evaluation

Six-week old female Carworth CF-1 mice, averaging 18 to 21 grams in weight, are placed ten to a cage and fed Purina Laboratory Chow ad libitum for 13 days. At the end of this feeding period, the mice are weighed and fed, for a 12-day period, diets containing the experimental compounds. At the end of the test feeding period, the mice are weighed and the gain for the period recorded. This gain is then compared to the gain of control animals. Experimental compounds are fed at from 200 ppm to 400 ppm in the diet. The diet used is reported below and data obtained are reported in Table I, where growth enhancement is reported as percent increase over controls. Control animals received the same diet as test animals but without test compound added.

Animals receiving test compound were generally noticeably larger than control animals and had better looking pelts than the control animals.

DIET

| | |
|---|---|
| Crude protein not less than | 23.0% |
| Crude fat not less than | 4.5% |
| Crude fiber not more than | 6.0% |
| Ash not more than | 9.0% |

INGREDIENTS

Meal and bond meal, dried skimmed milk, wheat germ meal, fish meal, animal liver meal, dried beet pulp, ground extruded corn, ground oat groats, soybean meal, dehydrated alfalfa meal, cane molasses, animal fat preserved with BHA, vitamin $B_{12}$ supplement, calcium pantothenate, choline chloride, folic acid, riboflavin supplement, brewers' dried yeast, thiamin, niacin, vitamin A supplement, D activated plant sterol, vitamin E supplement, calcium carbonate, dicalcium phosphate, iodized salt, ferric ammonium citrate, iron oxide, manganous oxide, cobalt carbonate, copper oxide, zinc oxide.

TABLE 1

Growth Enhancement Evaluations in Mice Obtained with Compounds having the Structure:

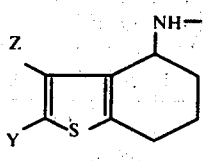

| X | Y | Z | $R_1$ | $R_2$ | Drug Concentration in Diet (ppm) | % Weight Gain Over Controls |
|---|---|---|---|---|---|---|
| O | H | H | H | H | 400 | 119.6 |
| O | H | H | $OCH_3$ | H | 400 | 68.5 |
| O | H | H | $CH_3$ | $CH_3$ | 400 | 55.1 |
| O | H | H | $OCH_3$ | $CH_3$ | 400 | 106.8 |
| O | H | H | OH | H | 400 | 102.9 |
| O | H | H | $CH(CH_3)_2$ | H | 400 | 88.0 |
| S | H | H | H | $C_2H_5$ | 400 | 54.6 |
| O | Br | H | H | H | 400 | 76.3 |
| O | H | H | $CH_2CH_2$—⟨phenyl⟩ | H | 400 | 72.3 |
| O | H | H | H | $CH_3$ | 400 | 104.9 |
| O | H | H | $CH_2$—$CH=CH_2$ | H | 400 | 48.4 |
| O | H | H | H | $C_2H_5$ | 200 | 87.6 |
| S | H | H | H | $CH_3$ | 400 | 88.5 |
| O | H | H | OH | $CH_3$ | 400 | 49.6 |

EXAMPLE 41

Growth Enhancement and Feed Efficiency Evaluations in Sheep Given an Implant Containing Test Compound To determine the effect of a 4,5,6,7-tetrahydrobenzo[b]thien-4-ylurea compound on sheep, Wether lambs are randomly allotted to pens in groups of six. The sheep are weighed and permitted food and water ad libitum. The feed is weighed daily, and uneaten feed from the previous day is collected and weighed. Test lambs receive the same unmedicated diet as control animals, but test animals receive one or more subcutaneous implants containing test compound at the base of the ear. The formulation of the implant used is given below. At the end of the six-week treatment period, the lambs are again weighed, and total feed consumed is calculated.

In these tests, six replicates of six lambs each per treatment are used and each animal receives from about 11 mg. to 105 mg. of test compound.

Average six-week weight gains are presented in Table II and feed per pound of gain is presented in Table III. From these data it can be seen that lambs implanted with 11 mg. or 99 mg. of test compound showed approximately a 10% increase in weight gain over untreated controls six weeks after implantation. Feed utilization for the same period was also improved by about 5% over untreated controls.

| LAMB DIET | % |
|---|---|
| Ground Corn Cob | 15.0 |
| Soybean Oil Meal (49%) | 10.0 |
| Dehydrated Alfalfa Meal | 15.0 |
| Molasses | 10.0 |
| Iodized Salt | 0.5 |
| Dicalcium Phosphate | 1.0 |
| Premix | 0.5 |
| | 100.0 |

Premix for One Ton

| | | |
|---|---|---|
| Tra-Min No. 3[1] | 454 | grams |
| Vitamin A (30,000 µ/g) | 133 | |
| Vitamin $D_3$ (200,000 µ/g) | 5 | |
| Corn Oil | 100 | |
| Ground Corn | 3848 | |
| | 4540 | |

| [1]Tra-Min No. 3: | Calcium | 21.00% |
|---|---|---|
| | Manganese | 12.50% |
| | Iron | 6.00% |
| | Zinc | 5.00% |
| | Copper | 0.65% |
| | Iodine | 0.35% |
| | Cobalt | 0.25% |

| Pellet Implant | |
|---|---|
| 4,5,6,7-Tetrahydrobenzo[b]thien-4-ylurea | 11.0 mg. |
| Glyceryl 12-hydroxy-stearate | 10.50 mg. |
| Magnesium stearate | 0.50 mg. |
| | 22.00 mg. |

TABLE II

| Treatment | Number Drug Implants[a] | Average Six-Week Weight Gain (kg./Lamb) Replication | | | | | | |
|---|---|---|---|---|---|---|---|---|
| | | 1 | 2 | 3 | 4 | 5 | 6 | Average |
| Control | 0 | 8.50 | 8.70 | 9.93 | 6.50 | 7.03 | 6.75 | 7.90 |
| 4,5,6,7-tetrahydrobenzo[b]thien-4-ylurea | 1 | 11.25 | 9.32 | 9.20 | 8.63 | 8.05 | 6.68 | 8.86 |
| | 9 | 10.83 | 9.60 | 8.75 | 7.20 | 8.53 | 7.20 | 8.69 |

[a]Approximate weight: 22 mg. each
Composition: 50% drug + 50% castorwax

TABLE III

| Treatment | Number Drug Implants[a] | Average Six-Week Feed/Gain per Pen Replication | | | | | | |
|---|---|---|---|---|---|---|---|---|
| | | 1 | 2 | 3 | 4 | 5 | 6 | Average |
| Control | 0 | 7.88 | 6.77 | 7.41 | 8.82 | 9.18 | 8.16 | 8.04 |
| 4,5,6,7-tetrahydrobenzo[b]thien-4-ylurea | 1 | 6.63 | 6.58 | 7.41 | 8.21 | 8.05 | 8.49 | 7.57 |
| | 9 | 6.51 | 6.75 | 7.80 | 8.38 | 7.56 | 7.97 | 7.49 |

[a]Approximate weight: 22 mg. each
Composition: 50% drug + 50% castorwax

What is claimed is:

1. A compound of the formula:

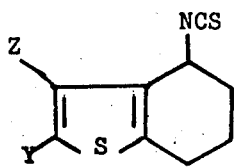

wherein Y is a member selected from the group consisting of hydrogen, halogen, and alkyl $C_1$–$C_4$, and Z is a member selected from the group consisting of hydrogen and alkyl $C_1$–$C_4$.

2. The compound according to claim 1, 4,5,6,7-tetrahydrobenzo[b]thien-4-yl isothiocyanate.

3. The compound according to claim 1, 2-methyl-4,5,6,7-tetrahydrobenzo[b]thien-4-yl isothiocyanate.

4. The compound according to claim 1, 3-methyl-4,5,6,7-tetrahydrobenzo[b]thien-4-yl isothiocyanate.

5. The compound according to claim 1, 2,3-dimethyl-4,5,6,7-tetrahydrobenzo[b]thien-4-yl isothiocyanate.

6. The compound according to claim 1, 2-bromo-4,5,6,7-tetrahydrobenzo[b]thien-4-yl isothiocyanate.

7. The compound according to claim 1, 2-chloro-4,5,6,7-tetrahydrobenzo[b]thien-4-yl isothiocyanate.

* * * * *